United States Patent [19]
Mihara et al.

[11] Patent Number: 5,902,730
[45] Date of Patent: May 11, 1999

[54] REAGENT FOR CALCIUM ION LEVEL DETERMINATION

[75] Inventors: Tatsuya Mihara; Hitoshi Kondo; Kazuhiko Nagata, all of Kyoto, Japan

[73] Assignee: Unitika Ltd., Hyogo, Japan

[21] Appl. No.: 08/053,701

[22] Filed: Apr. 29, 1993

Related U.S. Application Data

[63] Continuation of application No. 07/795,018, Nov. 20, 1991, abandoned.

[30] Foreign Application Priority Data

Nov. 20, 1991 [JP] Japan ................................. 2-316408

[51] Int. Cl.$^6$ ........................................................ C12Q 1/42
[52] U.S. Cl. .................................................................. 435/21
[58] Field of Search ................................................ 435/21

[56] References Cited

U.S. PATENT DOCUMENTS 4,223,090  9/1980  Mazza ........................................ 435/19

FOREIGN PATENT DOCUMENTS 2737287  2/1978  Germany ................................. 435/19

OTHER PUBLICATIONS

European Search Report.
Patent Abstracts of Japan, vol. 12, No. 47 (C–475)(2894) Feb. 12, 1988 & JP–A–62 195 297.
(Unitika Ltd) Aug. 28, 1987.
Fresenius Zeitschrift fur Analytische Chemie, vol. 308, No. 1, Aug.1, 1982, Berlin Brd, pp. 17–20.
M. Sugawara et al.: "Surface tension titration of metal ions by using metal salts of fatty acids as surface–active indicators".
Murachi, T. et al. Reagents Containing Lecithin in *Chem. Abs.* 108: 71690, 1988.
Kido, T et al. Use of Phospholipase D in *Chem. Abs.* 105: 13027, 1986.

*Primary Examiner*—Ralph Gitomer
*Attorney, Agent, or Firm*—Sughrue, Mion, Zinn, Macpeak & Seas

[57] ABSTRACT

A reagent for calcium ion level determination comprising a phospholipid, phospholipase D, choline oxidase, a surfactant and a divalent metal salt. The reagent can easily be prepared and with which quantitative determination of calcium ion can be made over a broad range of a calcium ion concentration with ease and accuracy in a continuous manner.

8 Claims, 4 Drawing Sheets

REAGENT FOR CALCIUM ION LEVEL DETERMINATION

This is a continuation of application Ser. No. 07/795,018 filed Nov. 20, 1991 now abandoned.

FIELD OF THE INVENTION

This invention relates to a reagent for quantitatively determining a calcium ion in body fluids such as blood and urine.

BACKGROUND OF THE INVENTION

In the field of clinical examinations, calcium ions in body fluids such as blood and urine are quantitatively analyzed for diagnosis of endocrine disorders such as parathyroid abnormality, circulatory diseases such as hypertension and arteriosclerosis, and the like. Quantitative analysis of calcium ions is roughly divided into two methods: one is an instrumental analysis exemplified by atomic-absorption spectroscopy and electrode method; and the other is chelate color formation exemplified by orthocresolphthalein complexone (hereinafter abbreviated as OCPC) method. In recent years, enzyme methods for calcium analysis have been proposed, in which activation or inhibition of an enzyme by calcium is utilized. For example, JP-A-62-195297 (the term "JP-A" as used herein means an "unexamined published Japanese patent application") discloses an analytical composition which utilizes the activation of phospholipase D by calcium ions; JP-A-62-36199 discloses an analytical composition which utilizes activation of calmodulin by calcium and activation of a calmodulin-dependent enzyme by the thus activated calmodulin; and JP-A-1-231896 discloses an analytical composition which utilizes activation of phospholipase $A_2$ by calcium ions. JP-A-2-142498 proposes an analytical composition which utilizes inhibition of pyruvate kinase by calcium ions. JP-A-2-276597 proposes a determination method using activation of amylase calcium ions.

The above-described instrumental analyses give relatively accurate values but require expensive instruments and complicated operations. In particular, atomic-absorption spectroscopy requires dilution of a sample under analysis, and the dilution operation causes errors in measurement.

Chelate color formation typically including OCPC is widely used for reasons that measurements can be made with a simple calorimeter, requiring neither special analytical instruments nor dilution operation. However, the results obtained include considerable factors of error because, for one thing, the degree of color formation is dependent on temperature, pH, etc. and, for another thing, specificity to calcium ions is not sufficient for avoiding influences of other co-present substances.

The up-to-date enzymatic methods have a narrow range of calcium analysis or easily are influenced by substances which are co-present and therefore lack reproducibility. For example, the method of using calmodulin (JP-A-62-36199) is disadvantageous in that calmodulin is hardly available, the measurable range of calcium concentration is narrow so that dilution of a sample is needed, and the two-stage activation system requires a long reaction time. The method of using phospholipase $A_2$ (JP-A-1-231896) and the method of using pyruvate kinase (JP-A-2-142498) cause errors when applied to assay of serum because these enzymes are present in blood. Besides, the method of using pyruvate kinase has poor accuracy since it utilizes enzyme inhibition by calcium ions. Further, the method of using amylase (JP-A-2-276597) has a problem in reproducibility of determined value since blank reaction is too large. The method of using phospholipase D (JP-A-62-195297) accomplishes measurements with accuracy because the enzyme used is not present in blood, but still is influenced by co-present salts and, in addition, is unsuitable for continuous measurements.

SUMMARY OF THE INVENTION

An object of the present invention is to provide a reagent for calcium ion level determination which can be easily prepared and with which quantitative determination of calcium ions can be made over a wide range of calcium ion concentrations with ease and accuracy.

As a result of extensive investigation, the inventors have found that a reagent comprising a phospholipid, phospholipase D, choline oxidase, a surfactant, and a divalent metal salt develops color to a degree proportional to the calcium ion concentration in a sample and makes it possible to quantitatively determine a wide range of calcium ion concentrations with accuracy in a continuous manner.

Thus, the present invention provides a reagent for calcium ion level determination comprising a phospholipid, phospholipase D, choline oxidase, a surfactant, and a divalent metal salt.

The present invention makes it possible to quantitatively determine the calcium ion level in body fluids in a continuous manner through simple operation and with high accuracy. In particular, addition of a divalent metal salt and a surfatant greatly broadens the detectable limit of calcium ions, excludes the influences of salts or other metallic ions present in body fluid samples, and makes continuous analysis feasible, thus bringing about remarkable improvements of performance properties of a reagent for quantitative calcium ion determination. In addition, the determination system of the present invention is applicable to automatic analyzers. Thus, the present invention provides an advantageous reagent which has never been developed in the field of clinical examination.

DETAILED DESCRIPTION OF THE INVENTION

Figure 1:
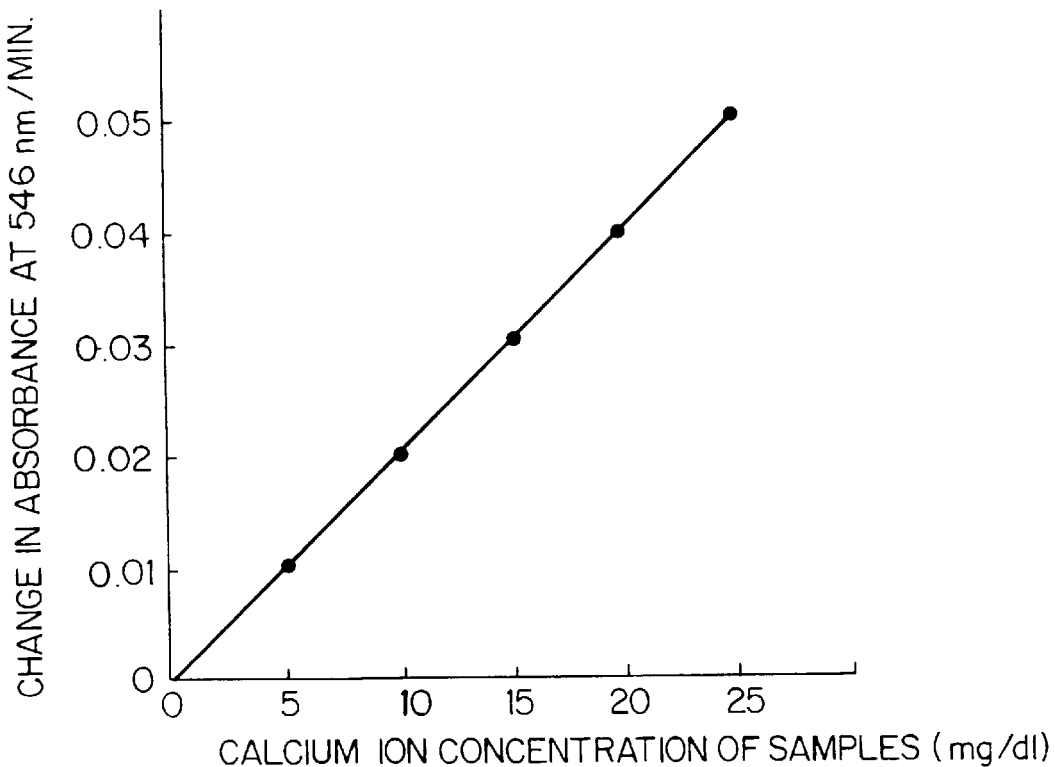
FIGS. 1, 5 and 6 show the determination ability of the reagent of the invention, wherein change per minute in absorbance at 546 nm is plotted as the ordinate and calcium ion concentration is plotted as the abscissa.

Phospholipids which can be used in the present invention are not particularly limited as long as they contain choline as a base moiety thereof. Examples of usable phospholipids are lysolecithin obtained from egg yolk, bovine liver, etc. such as L-α-lysophosphatidyl choline, L-α-lysophosphatidly choline palmitoyl and L-α-lysophosphatidyl choline stearoyl, lecithin obtained from egg yolk, soy beans, etc., and sphingomyelin obtained from egg yolk, bovine brain, etc. Preferred of them is egg yolk-origin lysolecithin because of its availability, excellent water solubility, and stable quality.

Phospholipase D is not limited in origin. For example, phospholipase D of animal (e.g., swine pancreas, rat brain) or plant origin (e.g., cabbage, carrot, peanut, spinach, cotton) or of microorganism origin (e.g., Streptomyces sp.). From the standpoint of stability, availability, and small scatter among production lots, phospholipase D of microorganism origin is preferred.

Choline oxidase is not limited in origin. For example, choline oxidase of microorganism origin, e.g., *Arthrobacter globiformis* or Alcaligenes sp., can be used.

Surfactants which can be used in the present invention include nonionic surfactants and anionic surfactants. Examples of nonionic surfactants include polyoxyethylene octylphenyl ester (e.g., Tritox X-100), sorbitan monolaurate (Span 20), sorbitan monopalmitate (Span 40), polyoxyethylene lauryl ester (Brij 35), polyoxyethylene cetyl ester (Brij 58), polyoxyethylenesorbitan monolaurate (Tween 20), polyoxyethylenesorbitan monopalmitate (Tween 40), polyoxyethylenesorbitan monooleate (Tween 80) and polyoxyethylenesorbitan monostearate (Tween 60). Examples of anionic surfactants include sodium laurylsulfate, sodium laurylbenzenesulfonate, sodium cholate, sodium deoxycholate and sodium laurylsarcosinate. These surfactants may be used either individually or in combination of two or more thereof. From the viewpoint of the effect of preventing white turbidity, fluidity at low temperatures, availability, and ease of preparation, a combination of Triton X-100, sodium laurylsulfate, and sodium laurylbenzenesulfonate and a combination of sodium deoxycholate, Triton X-100, and sodium laurylbenzenesulfonate are preferred.

Suitable divalent metal salts which can be used include divalent alkaline earth metal salts such as those of barium, divalent transition metal salts such as those of zinc, manganese, and the like. Suitable divalent salts include those which are soluble in aqueous solution such as the chlorides, the sulfates, and the like.

If desired, the reagent of the present invention may further contain generally employed additives and buffers. Especially, the additives which can be contained in the reagent include, for example, monovalent metal salt such as chloride, sulfate and acetate of sodium, potassium, etc., sugar such as sucrose and lactose, sugar alcohol such as sorbitol and mannitol, and protein such as bovine serum albumin. Buffers which can be used in the invention include those capable of buffering to a pH within the range of 5 to 9, such as tris(hydroxymethyl)aminomethane, N-tris(hydroxymethyl)methylglycine, N-2-hydroxyethylpiperazine-N'-propanesulfonic acid, N-2-hydroxyethylpiperazine-N'-ethanesulfonic acid, N-tris(hydroxymethyl)methyl-2-aminoethanesulfonic acid, N,N'-bis(2-hydroxyethyl)-2-aminoethanesulfonic acid, 3-(N-morpholine)propanesulfonic acid, piperazine-N,N'-bis(2-ethanesulfonic acid) and bis(2-hydroxyethyl)imino-tris-(hydroxymethyl)methane.

In preferred embodiments of the present invention, the reagent contains from 0.2 to 100 mg/ml, preferably from 0.5 to 50 mg/ml, of lysolecithin; from 0.0001 to 1.0 U/ml, preferably from 0.0005 to 1.0 U/ml, of phospholipase D; from 0.1 to 50 U/ml, preferably from 0.1 to 15 U/ml, of choline oxidase; from 0.001 to 5% by weight, preferably from 0.01 to 0.5% by weight, of Triton X-100, from 0.001 to 5% by weight, preferably from 0.01 to 0.5% by weight, of sodium laurylsulfate; from 0.001 to 5% by weight, preferably from 0.01 to 0.5% by weight, of sodium laurylbenzenesulfonate; and from 0.1 to 200 mM, preferably from 0.5 to 100 mM, of a divalent metal salt. A buffer is added so as to adjust to a pH of from 4.0 to 10.0 and to a concentration of from 1 to 1000 mM. It is particularly preferred to adjust the pH within the range of 5.0 to 9.0 and the concentration within the range of 10 to 500 mM.

The principle of the calcium ion determination by use of the reagent according to the present invention will be illustrated below taking the instance of using lecithin (lysolecithin) as a phospholipid.

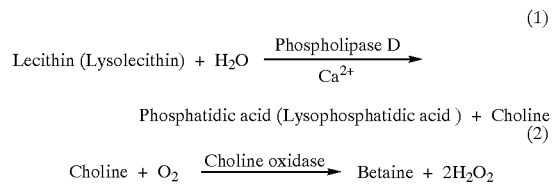

(1)

(2)

In reaction formula (1), manifestation of activity of phospholipase D essentially requires the presence of calcium ions, and the activity of phospholipase D increases in proportion to the calcium ion concentration. The presence of a divalent metal salt in this reaction system produces an effect of greatly broadening the calcium ion measurable range. Further, the presence of a surfactant in the system is effective to prevent the reagent from becoming turbid, to greatly increase measurement sensitivity, and to stabilize the phospholipase D reaction.

Calcium ion determination is accomplished by quantitatively determining $H_2O_2$ finally produced in formula (2) by means of a hydrogen peroxide electrode, or by reacting $H_2O_2$ with peroxidase in the presence of an appropriate color reagent and calorimetrically analyzing the color change. Requiring no special instrument, the latter method is especially suitable for daily examinations. The principle of the latter method is illustrated below.

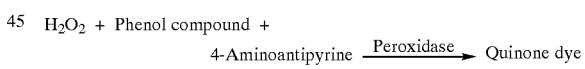

Peroxidase used in the above color reaction includes one obtained from horseradish. Peroxidase is used in a concentration of from 0.1 to 300 U/ml, and preferably from 0.5 to 200 U/ml.

Phenol compounds to be used here include phenol, toluidine, aniline, and derivatives of these compounds. The phenol compound is used in a concentration of from 0.01 to 20% by weight, and preferably from 0.1 to 10% by weight.

Color reagents to be used include, for example, 4-aminoantipyrine. It is used in an amount of from 0.001 to 10% by weight, and preferably from 0.01 to 5% by weight. A buffer is added so as to adjust to pH 4.0 to 10.0, and particularly 5.0 to 9.0, and to a concentration of 1 to 1,000 mM, and particularly 10 to 500 mM.

In carrying out calcium ion determination by use of the reagent of the present invention, a reagent solution containing phospholipase D, choline oxidase, a surfactant, a color reagent, and other additives is previously mixed with a sample under analysis, and the mixture is preliminarily heated to a temperature within the a range of 25 to 37° C. Then, a reagent solution containing a divalent metal salt, a phospholipid, peroxidase, a surfactant, a phenol compound, and other additives is added thereto, and the rise of absorbance rate is measured at a wavelength arbitrarily selected within the range of from 500 to 640 nm according to the choice of the phenol compound and the color reagent. Alternatively, a reagent solution containing a divalent metal salt, a phospholipid, choline oxidase, a surfactant, a color reagent, and other additives is previously mixed with a sample under analysis, and the mixture is preliminarily heated to a temperature appropriately selected from 25 to 37° C. Then, a reagent solution containing phospholipase D, peroxidase, a surfactant, a phenol compound, and other additives is added thereto, and the rate increase of absorbance is measured at a wavelength arbitrarily selected within the range of from 500 to 640 nm according to the choice of the phenol compound and the color reagent.

The present invention is now illustrated in greater detail with reference to Examples, but it should be understood that the present invention is not deemed to be limited thereto. Unless otherwise indicated herein, all parts, percents, ratios and the like are by weight.

EXAMPLE 1

Reagent solutions (I) and (II) having the following composition were prepared. The reagents other than those specified by origin or maker were commercially available guaranteed reagents.

| Reagent Solution (I): | |
| --- | --- |
| N-tris(Hydroxymethyl)ethyl-2-amino-methanesulfonic acid (purchased from Dojindo Laboratories, hereinafter abbreviated as TES) buffer (pH = 7.4) | 140 mM |
| Phospholipase D (origin: *Streptomyces chromofuscus*; purchased from Boehringer Mannheim Yamanouchi Co., Ltd.) | 0.02 U/ml |
| Choline oxidase (origin: Alcaligenes sp.; purchased from Toyobo Co., Ltd.) | 10.5 U/ml |
| 4-Aminoantipyrine | 0.25 mg/ml |
| Triton X-100 | 0.02 w/v % |
| Reagent Solution (II): | |
| TES buffer (pH = 7.4) | 140 mM |
| Lysolecithin (origin: egg yolk; purchased from Sigma Chemical Co.) | 4.3 mg/ml |
| MnCl$_2$ | 14.4 mM |
| Peroxidase (origin: horseradish; purchased from Toyobo Co., Ltd.) | 16.8 U/ml |
| N-Ethyl-N-2-hydroxyethyl-m-toluidine (purchased from Tokyo Kasei Kogyo Co., Ltd.; hereinafter abbreviated as EHET) | 1 mg/ml |
| Sodium laurylsulfate | 0.11 w/v % |
| Sodium laurylbenzenesulfonate | 0.11 w/v % |
| Triton X-100 | 0.20 w/v % |

To 320 μl of reagent solution (I) was added 20 μl of a standard sample of known calcium ion concentration, and the mixture was preliminarily heated at 37° C. Then, 250 μl of reagent solution (II) was added thereto, and the change in absorbance at 546 nm per minute was measured at 37° C.

Figure 2:
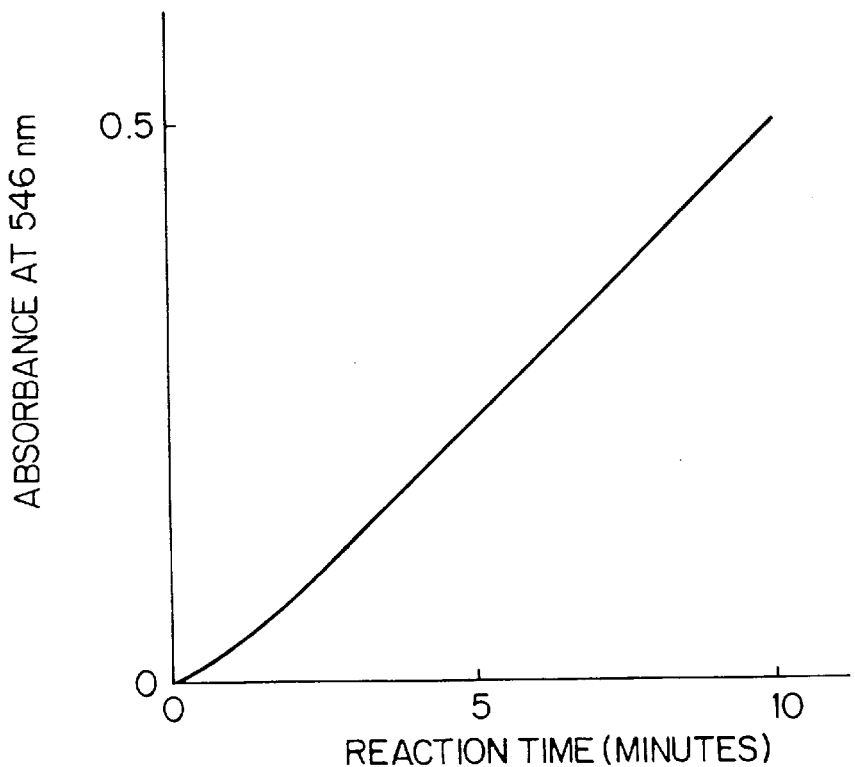
FIG. 2 is a graph showing change in absorbance at 546 nm with time in the determination of calcium ion level using the reagent of the invention, wherein absorbance at 546 nm is plotted as the ordinate and time is plotted as the abscissa.

As shown in FIG. 1, the reagent of the present invention gives a satisfactorily straight line. It was also confirmed that the reaction linearly proceeds with time as shown in FIG. 2.

Figure 3:
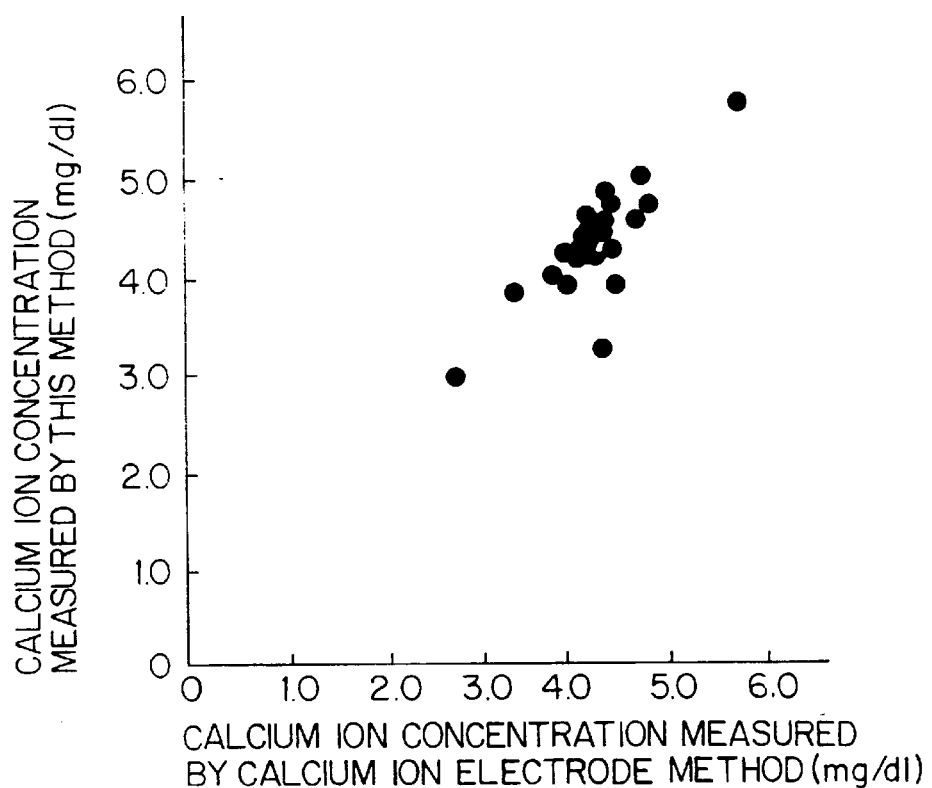
FIG. 3 shows the relationship between measured values obtained by ion electrode method as the abscissa and those obtained by the reagent of the invention as the ordinate.

For reference, standard samples with a concentration of 3 to 6 mg/dl were analyzed using either the above reagent of the invention or a calcium ion electrode method. The results obtained are plotted in FIG. 3. It is apparent from FIG. 3 in view of FIG. 1 that the data obtained by the present invention are in good agreement with those obtained by the electrode method.

COMPARATIVE EXAMPLE 1

Figure 4:
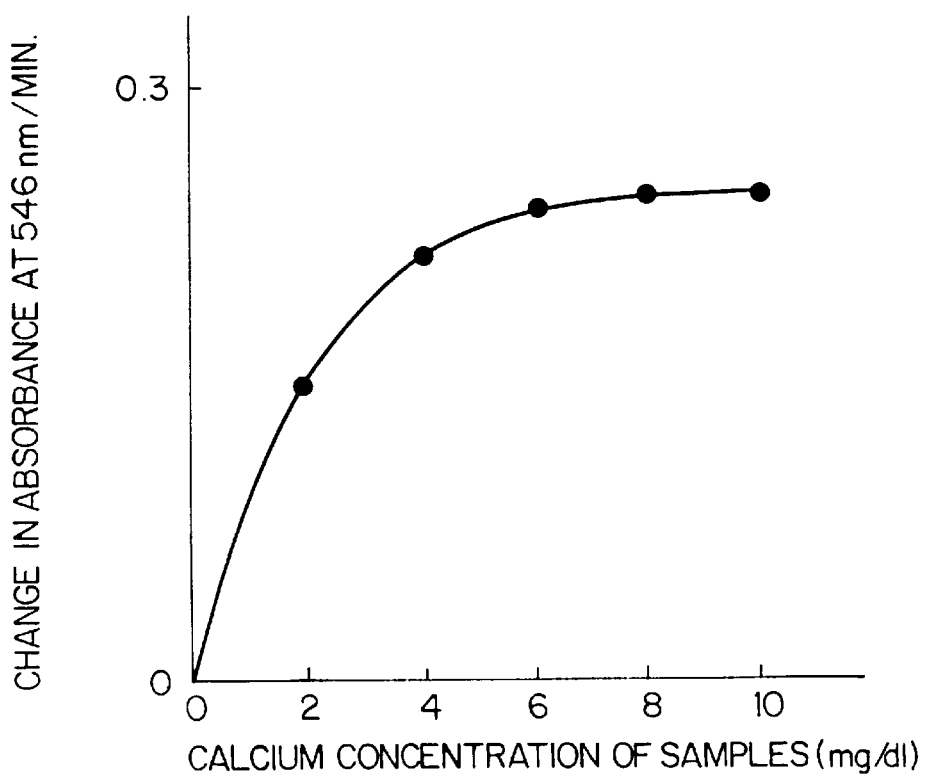
FIG. 4 shows the determination ability of the reagent without a divalent metal salt, wherein change per minute in absorbance at 546 nm is plotted as the ordinate and calcium ion concentration in the sample is plotted as the abscissa.

Calcium ion level determination was carried out in the same manner as in Example 1, except that reagent solution (II) contains no MnCl$_2$. The result obtained is shown in FIG. 4. It is apparent that the comparative reagent system failed to give data forming a straight line.

EXAMPLE 2

In order to prove applicability of lecithin as a substrate, calcium ion level determination was carried out in the same manner as in Example 1, except for the use of the following reagent solutions. Lecithin of egg yolk origin was purchased from Sigma Chemical Co. Other reagents used are the same as those used in Example 1.

| Reagent Solution (I): | |
| --- | --- |
| TES buffer (pH = 7.4) | 138 mM |
| Lecithin | 6 mg/ml |
| MnCl$_2$ | 10 mM |
| Choline oxidase (Alcaligenes sp.) | 9.3 U/ml |
| 4-Aminoantipyrine | 0.22 mg/ml |
| Sodium laurylsulfate | 0.28 w/v % |
| Sodium deoxycholate | 0.28 w/v % |
| Triton X-100 | 0.75 w/v % |
| Reagent Solution (II): | |
| TES buffer (pH = 7.4) | 142 mM |
| Phospholipase D (*Streptomyces chromofuscus*) | 0.03 U/ml |
| Peroxidase (horseradish) | 20 U/ml |
| EHET | 1 mg/ml |

Figure 5:
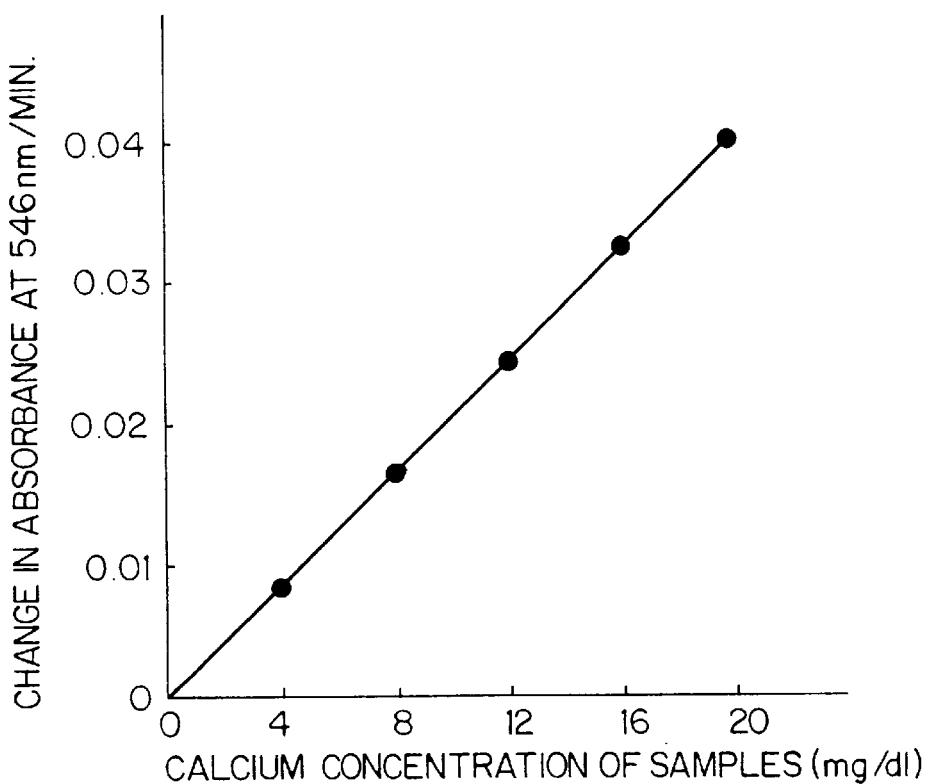

The results obtained are shown in FIG. 5, in which a plot of calcium ion concentration vs. rate of change in absorbance gave a straight line (up to 20 mg/dl).

EXAMPLE 3

In order to prove applicability of zinc chloride as a divalent metal salt, calcium ion level determination was carried out in the same manner as in Example 1, except for using the following reagent solutions.

| Reagent Solution (I): | |
| --- | --- |
| TES buffer (pH = 7.4) | 138 mM |
| Lysolecithin | 3 mg/ml |
| ZnCl$_2$ | 66 mM |
| Choline oxidase (Alcaligenes sp.) | 9.3 U/ml |
| 4-Aminoantipyrine | 0.22 mg/ml |
| Sodium laurylsulfate | 0.08 w/v % |
| Sodium laurylbenzenesulfonate | 0.08 w/v % |
| Triton X-100 | 0.08 w/v % |
| Reagent Solution (II): | |
| TES buffer (pH = 7.4) | 142 mM |
| Phospholipase D (*Streptomyces chromofuscus*) | 0.3 U/ml |
| Peroxidase (horseradish) | 20 U/ml |
| EHET | 1 mg/ml |

Figure 6:
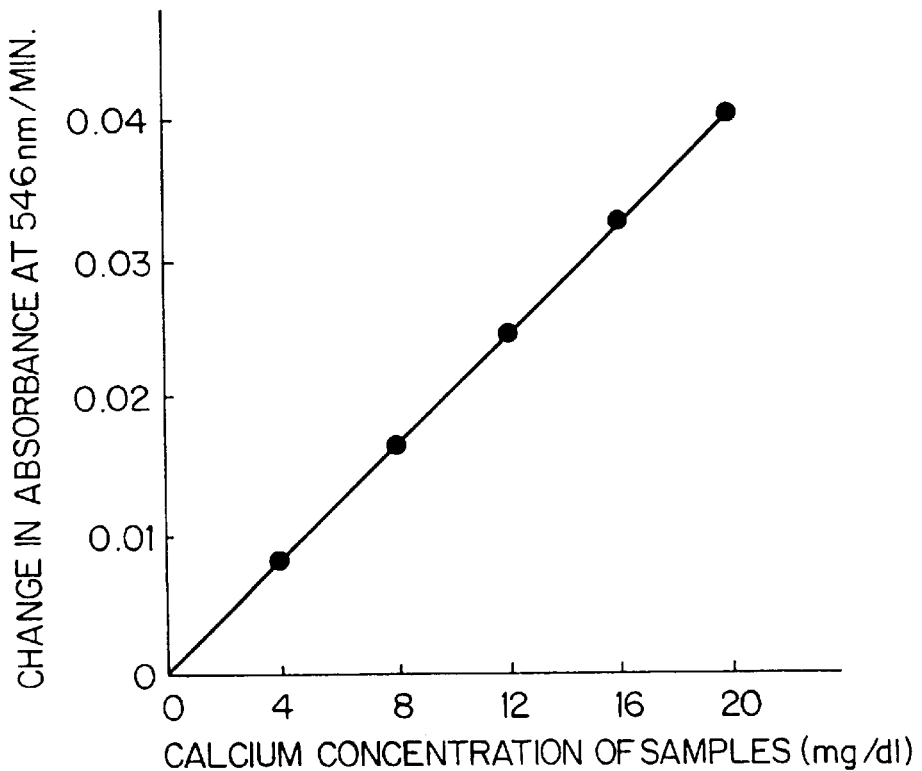

The results obtained are shown in FIG. 6, in which a plot of calcium concentration vs. rate of change in absorbance gave a straight line (up to 20 mg/dl).

EXAMPLE 4

A calcium ion solution of 0, 10 or 20 mg/dl was prepared, containing 0 to 29 mg/dl magnesium ion, 0 to 1.1 mg/dl manganese ion, 0 to 1.3 mg/dl copper ion, 0 to 1.3 mg/dl zinc ion, 0 to 1.1 mg/dl iron ion, 0 to 2.7 mg/dl barium ion, 0 to 1.4 mg/dl lithium ion, 0 to 2,000 mg/dl potassium ion and 0 to 1,200 mg/dl sodium ion.

Next, reagents of the following composition were prepared.

| Reagent Solution (I): | |
| --- | --- |
| TES buffer (pH = 7.4) | 140 mM |
| Phospholipase D (*Streptomyces chromofuscus*) | 0.022 U/ml |
| Peroxidase (horseradish) | 12.0 U/ml |
| EHET | 0.6 mg/ml |
| Bovine serum albumin (Boehringer Mannheim Yamanouchi Co., Ltd.) | 0.052 w/v % |
| Triton X-100 | 0.022 w/v % |
| Reagent Solution (II): | |
| TES buffer (pH = 7.4) | 140 mM |
| Lysolecithin | 4.63 mg/ml |
| $MnCl_2$ | 16 mM |
| Choline oxidase (*Arthrobacter globioformis*, Toyo Jozo Co., Ltd.) | 14.7 U/ml |
| 4-Aminoantipyrine | 0.35 mg/ml |
| Sodium laurylsulfate | 0.13 w/v % |
| Sodium laurylbenzenesulfonate | 0.13 w/v % |
| Triton X-100 | 0.23 w/v % |
| Bovine serum albumin | 0.033 w/v % |

The process of Example 1 was repeated to measure the change in the absorbance except that the reagent solution (I), the sample solution and the reagent solution (II), above prepared, were used in the amount of 300 μl, 15 μl and 200 μl, respectively.

Figure 7:
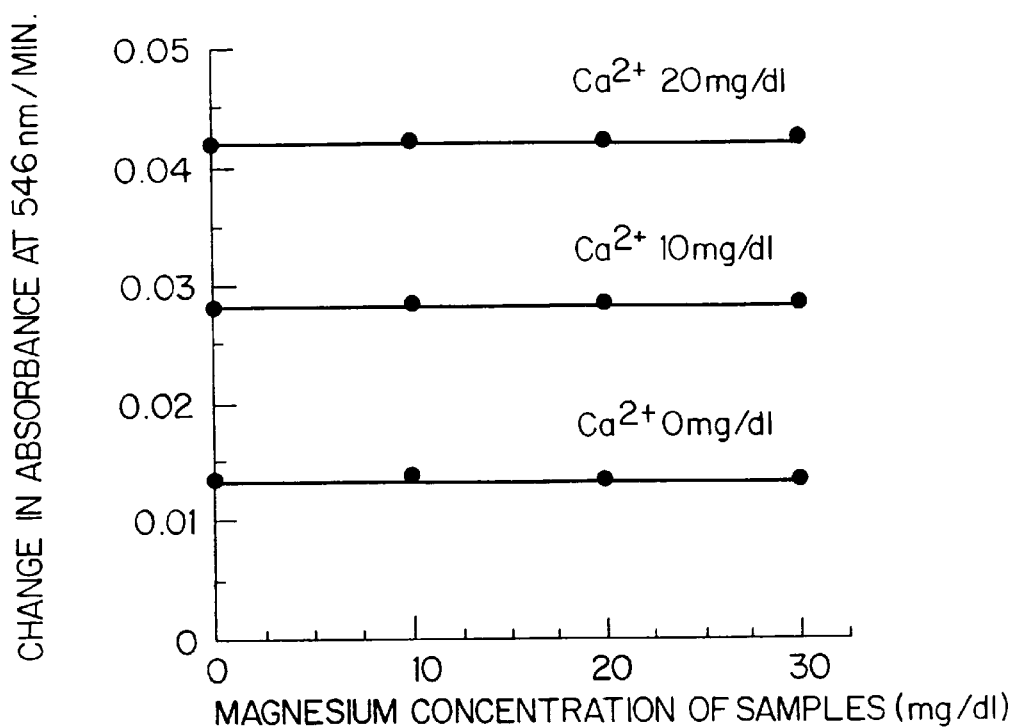
FIG. 7 shows effect of magnesium on the calcium determination using the reagent of the invention, wherein change per minute in absorbance at 546 nm is plotted as the ordinate and concentration of magnesium to be added to a sample is plotted as the abscissa.

The result obtained is shown in FIG. 7. It can be seen that the reagent of the present invention is not affected by magnesium ion (up to 29 mg/dl) at all.

Also, the reagent of the present invention is confirmed to have a good utility since manganese ion (1.1 mg/dl), copper ion (1.3 mg/dl), zinc ion (1.3 mg/dl), iron ion (1.1 mg/dl), barium ion (2.7 mg/dl), lithium ion (1.4 mg/dl), potassium ion (2,000 mg/dl) and sodium ion (1,200 mg/dl) did not affect the results.

EXAMPLE 5

A solution with calcium concentration of 10 mg/dl and 18 mg/dl was examined in 31 samples each, using a solution containing 10 mg/dl calcium as a standard in the same manner as in Example 4.

As a result, the average of the determined value were 10.26 mg/dl and 17.88 mg/dl and the standard deviation were 0.075 mg/dl and 0.112 mg/dl, respectively. The C.V. value is 0.73 % and 0.63 %, respectively, which is an indication of accuracy in determination calculated by the equation of (standard deviation÷mean determined value)× 100 (%). The reagent of the present invention appears to have accuracy sufficient for practical use.

EXAMPLE 6

Sixty samples of serum were examined using a solution containing 10 mg/dl calcium as a standard in the same manner as in Example 4. On the other hand, 60 samples of the same serum were also examined using a reagent for calcium ion level determination based on the typical conventional method of OCPC (available from Iaton Laboratories, Inc).

Figure 8:
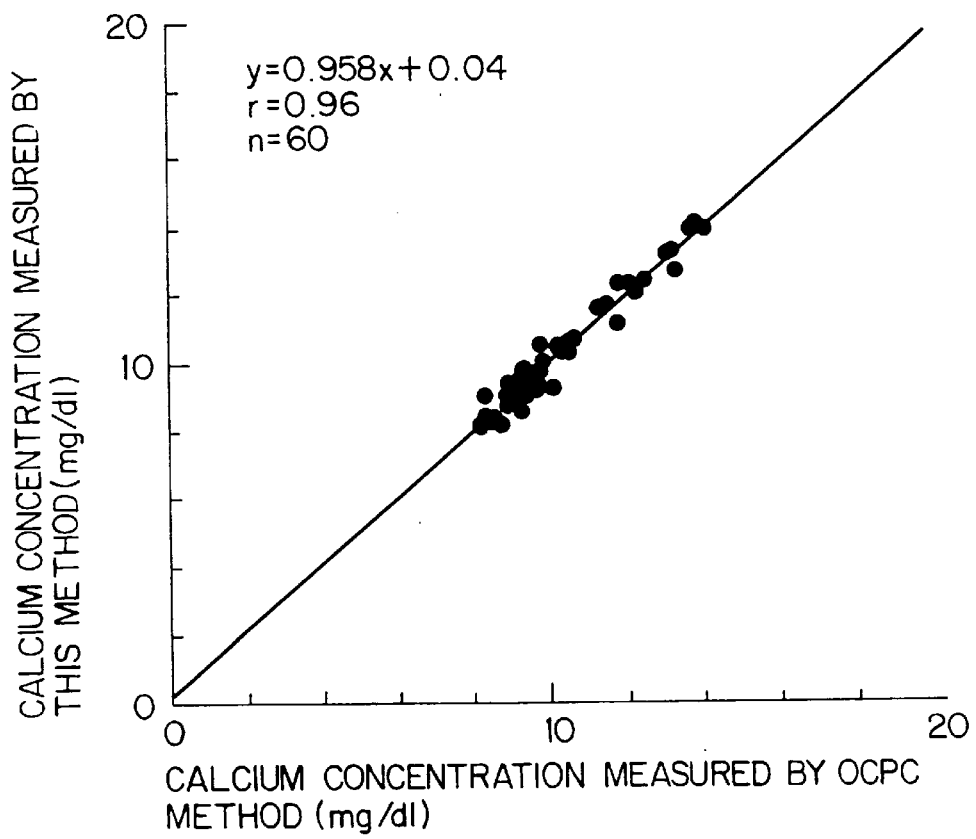
FIG. 8 shows relationship between the reagent of the invention and OCPC method, wherein the determined value by the reagent of the invention is plotted as the ordinate and those by OCPC method is plotted as the abscissa.

The relationship between the value obtained by the present reagent and the value obtained by the OCPC reagent is shown in FIG. 8. The regression straight line exhibits good relationship between them with n=60, r=0.96 and y=0.985x+ 0.04. The reagent of the present invention appear sufficiently accurate in practical use.

While the invention has been described in detail and with reference to specific examples thereof, it will be apparent to one skilled in the art that various changes and modifications can be made therein without departing from the spirit and scope thereof.

What is claimed is:

1. A reagent for determining the level of calcium ion in a sample, comprising a phospholipid with choline as a base moiety thereof, phospholipase D, choline oxidase, a surfactant, and a divalent metal salt other than calcium, wherein said reagent contains from 0.5 to 20 mg/ml of said phospholipid; from 0.0001 to 1.0 U/ml of said phospholipase D; from 0.1 to 50 U/ml of said choline oxidase; from 0.01 to 1% by weight of said surfactant; and from 0.1 to 200 mM of said divalent metal salt.

2. The reagent for determining the level of calcium ion as claimed in claim 1, wherein said divalent metal salt is a salt of a divalent alkaline earth metal or a salt of a divalent transition metal.

3. The reagent for determining the level of calcium ion as claimed in claim 2, wherein said divalent metal salt is a salt of barium, zinc or manganese.

4. The reagent for determining the level of calcium ion as claimed in claim 1, wherein said phospholipid is lysolecithin and/or lecithin.

5. The reagent for determining the level of calcium ion as claimed in claim 1, wherein said phospholipase D is obtained from the microorganisms of the genus Streptomyces.

6. The reagent for determining the level of calcium ion as claimed in claim 1, wherein said surfactant is a nonionic surfactant and/or an anionic surfactant.

7. The reagent for determining the level of calcium ion as claimed in claim 1, wherein the pH of the reagent ranges from 4 to 10.

8. The reagent for determining the level of calcium ion as claimed in claim 1, wherein said reagent additionally contains a buffer capable of buffering to a pH within the range of 5 to 9.

* * * * *